United States Patent [19]

Sauvinet et al.

[11] Patent Number: 4,859,499

[45] Date of Patent: Aug. 22, 1989

[54] METHOD FOR COATING A SUBSTRATE WITH AN ELECTRICALLY CONDUCTIVE LAYER

[75] Inventors: Vincent Sauvinet, Paris; Jean Bletry, Versailles; Micheline Bonnaud, Malakoff; Maurice Trouve, Nemours, all of France

[73] Assignee: Saint-Gobian Vitrage, Courbevoie, France

[21] Appl. No.: 821,365

[22] Filed: Jan. 22, 1986

[30] Foreign Application Priority Data

Jan. 22, 1985 [FR] France ................................ 85 00854
Jul. 3, 1985 [FR] France ................................ 85 10145

[51] Int. Cl.$^4$ .......................... B05D 5/12; B05D 5/06
[52] U.S. Cl. .................................... 427/108; 427/126.2; 427/126.3; 427/166; 427/168; 427/180; 427/201; 427/314; 427/380; 65/60.52
[58] Field of Search ............ 427/166, 201, 180, 255.2, 427/255.3, 248.1, 314, 168, 108, 380, 110, 126.2, 126.3; 428/432; 65/60.52

[56] References Cited

U.S. PATENT DOCUMENTS

| | | | |
|---|---|---|---|
| 3,666,534 | 5/1972 | Groth et al. ........................ | 427/168 |
| 3,676,729 | 7/1972 | Menelly ............................. | 427/64 |
| 3,949,259 | 4/1976 | Kostlin et al. ..................... | 427/168 |
| 4,172,159 | 10/1979 | Marcault ........................... | 427/160 |
| 4,252,841 | 2/1981 | Kinugawa et al. .................. | 427/108 |
| 4,263,335 | 4/1981 | Wagner et al. ..................... | 427/168 |
| 4,303,554 | 12/1981 | Sudo et al. ......................... | 427/110 |
| 4,325,988 | 4/1982 | Wagner .............................. | 427/168 |
| 4,344,986 | 8/1982 | Henery .............................. | 427/168 |
| 4,374,156 | 2/1983 | Vong .................................. | 427/168 |
| 4,533,571 | 8/1985 | Kramer et al. ..................... | 427/180 |
| 4,547,400 | 10/1985 | Middleton et al. ................. | 427/168 |
| 4,562,095 | 12/1985 | Coulon et al. ..................... | 427/180 |

FOREIGN PATENT DOCUMENTS 454198 2/1975 U.S.S.R. .

OTHER PUBLICATIONS

Chemical Abstracts, vol. 81, No. 24, Dec. 16, 1974, p. 645.

*Primary Examiner*—Janyce Bell
*Attorney, Agent, or Firm*—Pennie & Edmonds

[57] ABSTRACT

A method for coating a substrate, preferably of glass, with a pyrolyzed transparent, electroconductive layer. The coating is comprised of indium formate, optionally mixed with a powdered or gaseous tin compound or a gaseous organotin compound. The coating layer is deposited upon a hot substrate whereupon it pyrolytically decomposes, forming a layer which is subsequently heat treated in a reducing or an oxidizing atmosphere to optionally enhance the low emissivity and low resistivity of the coating or reduce said low emissivity and low resistivity properties.

26 Claims, 1 Drawing Sheet

U.S. Patent
Aug. 22, 1989
4,859,499
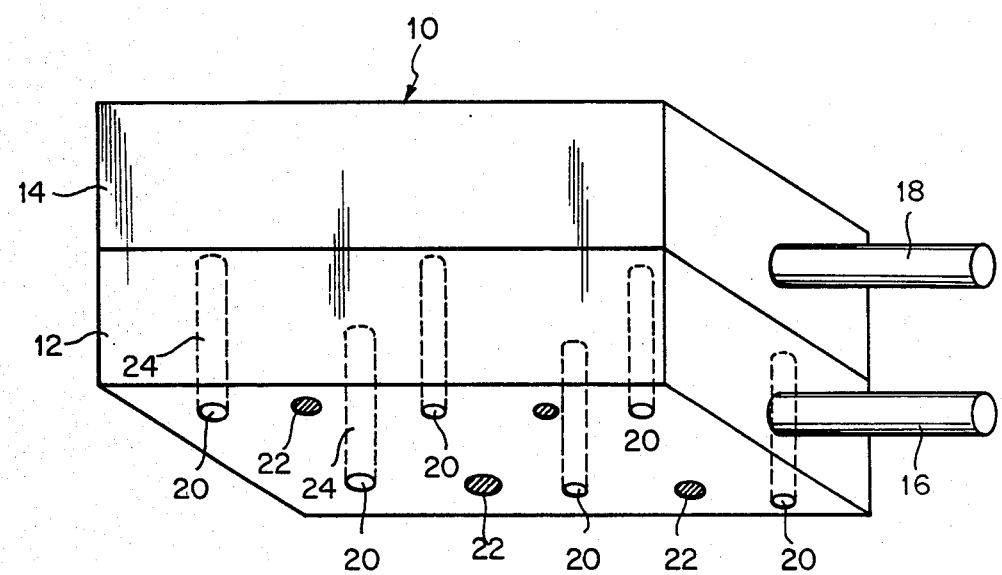

METHOD FOR COATING A SUBSTRATE WITH AN ELECTRICALLY CONDUCTIVE LAYER

TECHNICAL FIELD

This invention concerns the preparation of a metal based powder and a method for pyrolytically depositing it upon a substrate to form a transparent coating with low emissivity and good electrical conduction.

BACKGROUND ART

To enable a pulverulent metal compound to form a high quality coating on a substrate, the powder must be uniformly distributed, it must effectively decompose at a temperature below about 650°–700° C. if the substrate to be coated is glass and further, the compound must contain a sufficient proportion of metal so as to quickly form an oxide layer of appreciable thickness, particularly if the substrate is moving rapidly in relation to the powder distribution means, as is the case for a glass ribbon at the outlet of a float bath.

Coatings of tin oxide on glass substrates, produced by the pyrolysis of dibutyltin oxide (DBTO) or dibutyltin fluoride (DBTF) powders are frequently employed with a view to reinforcing the surface of the glass, staining it and for providing such surfaces with specific optical and/or electrical characteristics, most notably, low emissivity. The use of powdered DBTO to produce such coatings is disclosed in French Patent Application Nos. 2,380,997 and 2,391,966 whereas the use of DBTF is disclosed in European Patent No. 39,256 and French Patent Application No. 2,542,636.

While both dibutyltin oxide and dibutyltin fluoride powders are capable of forming satisfactory layers, such layers develop colored reflections when they are deposited in the thickness necessary to obtain advantageous electronic properties. Further difficulties arise because slight variations in the thickness of the layers causes color irregularities and further, the color which is produced is often either not aesthetically pleasing or it may not be adapted to the style of the surrounding structure.

In order to obtain perfect color uniformity the reaction conditions under which the DBTO and DBTF powders are deposited must be scrupulously monitored. In particular, the powder must be of a consistent high quality and the spraying mechanism utilized to distribute the coating must be precisely adjusted so as to deposit a constant amount of powder upon the substrate.

In order to prevent the development of colored films on glass substrates and to avoid the necessity of implementing stringent monitoring techniques which are both expensive and time-consuming, applicants have developed a method wherein a powder containing indium formate may be distributed upon a hot substrate such as a glass ribbon passing the output of a float bath and which, upon the resultant pyrolysis of the powder, forms a thin, transparent, electroconductive coating upon the substrate.

Moreover, the pyrolysis of the indium formate compound may be performed with a sufficiently high degree of efficiency so as to be compatible with the rapid passing of the substrate past the point at which the coating is produced. This is in contrast to prior attempts at depositing pyrolyzed indium compounds upon glass substrates wherein solubilized indium acetylacetonates were found to pyrolyze at speeds insufficient for depositing a metallic oxide coating on a glass ribbon passing the output of a float bath at high speed.

SUMMARY OF THE INVENTION

This invention concerns the preparation of a metal based powder and a method for pyrolytically depositing this powder upon a substrate in order to form a transparent coating with low emissivity and good electrical conduction.

A method for coating a substrate, such as glass, metal, ceramic or other refractory materials with a pyrolyzed metal oxide coating comprises depositing a predetermined amount of indium formate upon the surface of a heated substrate so as to pyrolyze the indium formate, thus forming a coating of indium oxide on the surface of the substrate.

The indium formate may be deposited upon the surface of the substrate as a powder or it may first be dissolved in a suitable solvent such as methyl alcohol prior to the deposition step.

Applicants have also developed a novel method of producing the necessary indium formate which comprises reacting an indium compound with an inorganic acid, such as hydrochloric or nitric acid to form an indium salt, reacting the indium salt with ammonia so as to form an indium hydroxide precipitate, washing and drying the resultant precipitate and reacting the indium hydroxide precipitate with formic acid so as to produce indium formate.

When the substrate is glass, such as a glass ribbon at the outlet of a float bath, the substrate should only be heated to a temperature below about 650°–700° C. prior to the deposition of the coating.

In an alternate embodiment of the method the indium formate may be mixed with at least one compound having a decomposition temperature on the same order as that of indium formate prior to depositing the composition onto the surface of the heated substrate. This compound may be a powdered tin compound such as dibutyltin oxide or dibutyltin fluoride, a gaseous tin compound such as $SnCl_4$ or a gaseous organotin compound such as $BuSnCl_3$. When powdered tin compounds are mixed with the indium formate, they are added in proportions ranging between about one and thirty percent by weight.

A further embodiment of the invention concerns a method for forming a transparent electroconductive coating on a substrate. The method comprises preparing a metal composition containing indium formate or a mixture of indium formate with one or more of the powdered or gaseous tin compounds or the gaseous organotin compound discussed above, depositing this composition onto the surface of a heated substrate, such as glass, metal, ceramic or other refractory material, in order to pyrolyze the composition and then heating the coated substrate to enhance the properties of the layer.

The coating may be deposited upon the substrate as a powder or it may first be dissolved in a suitable solvent such as methyl alcohol before being deposited. When the composition is to be deposited upon the substrate as a powder, it must first be suspended in a carrier gas and the carrier gas with the suspended powder particles is then directed against a surface of the substrate so as to deposit the powder upon the substrate.

There are various methods by which the coated substrate may be heated so as to enhance properties such as the transparency, emissivity and electrical conductivity of the coating. One method concerns maintaining the coated substrate in a heated enclosure for a predetermined period of time. The atmosphere in the enclosure may be a reducing atmosphere so as to promote the formation of a metal coating or to enhance the low emissivity and low conductivity properties of the coating or it may consist of an oxidizing atmosphere to increase the emissivity and conductivity of the coating.

Alternatively, the coated substrate may be heat treated by subjecting the coated surface of the substrate to an intense heat delivered by a burner tip of the type illustrated in the attached drawing figure for less than one second. The heat treatment may occur on the line for manufacturing coated glass or, out of this line at any time after the manufacture of said coated glass.

Alternately, preselected areas of the coating may be subjected to different degrees of heating so as to obtain a coating layer having portions with differing emissivity, transparency and electrical conductivity.

BRIEF DESCRIPTION OF THE DRAWING

Further benefits and advantages of the invention will become apparent from a consideration of the following description given with reference to the accompanying drawing figure which is a perspective view of a burner used to provide an intense heat of short duration according to one of the embodiments of the invention described herein.

DETAILED DESCRIPTION OF THE INVENTION

The present invention provides a method for preparing an indium formate powder as well as a method for depositing an electrically conductive coating containing indium formate upon a substrate such as a glass ribbon passing at high speed at the outlet of a float bath. Other possible substrates may include metals, ceramics or other refractory materials. By an electrically conductive coating, applicants mean a metal based coating comprising any compound whose thermal decomposition temperature is of the same order as indium formate.

While indium formate may be the sole metallic component of the powder used in the method of the invention, it may also be associated with one or more metallic constituents having a decomposition temperature on the same order as that of indium formate.

The process proposed herein for producing indium formate comprise reacting the indium with an acid such as hydrochloric acid (HCl), precipitating indium hydroxide by reacting the salt thus formed with ammonia at a temperature close to boiling, washing and then drying the precipitate and then reacting it with formic acid.

The reaction process may be summarized according to the following equations, utilizing, for example, hydrochloric acid to react with the indium:

$2In + 6 HCl \rightarrow 2InCl_3 + 3 H_2$ 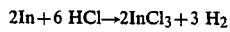

$InCl_3 + 3 NH_4OH \rightarrow In(OH)_3 + 3NH_4Cl$ 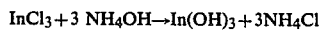

$In(OH)_3 + 3 HCOOH \rightarrow In (HCOO)_3 + 3H_2O$ 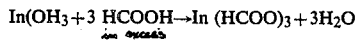

One skilled in the art will realize that various other acids, such as nitric acid (HNO$_3$) may be used in place of hydrochloric acid.

In order to obtain sufficiently conductive layers, it is advantageous to combine tin compounds with the indium formate powder, in particular dilutyltin fluoride (DBTF) and dibutyltin oxide (DBTO), in proportions that may range up to about 30 weight percent. These compounds actually serve as cationic dopants of the indium oxide because replacement of an indium atom with a tin atom introduces a free electron into the layer. The density of the charge carriers and the electrical conductivity of the layer are also concurrently increased due to this doping effect.

The indium formate powder or powder mixture may be sprayed on to a substrate, particularly a glass ribbon, with a nozzle. Examples of such nozzles are described in French Patent Application Nos. 2,542,636 and 2,542,637 preceded by the distribution device described in French Patent Application No. 2,548,556.

The doping may also be performed with gaseous compounds, such as SnCl$_4$ or gaseous organotins such as BuSnCl$_3$. When utilizing compounds of this type the powder must initially be suspended in a gas while the doping agent is subsequently mixed with the resultant suspension and/or with the gasses which serve as accelerants and/or homogenates of the powder. The doping agent chosen may also be aspirated by a nozzle arrangement found in a control chamber such as that disclosed in French Patent Application No. 2,542,636, and/or delivered at the exit of the nozzle by a special duct.

Subsequent to this pyrolytic deposition of the metallic oxide layer upon the substrate, the coated substrate advantageously undergoes a heat treatment in order to modify the properties of the coating. Depending upon the parameters chosen for this operation this treatment may either increase the number of oxygen holes in the coating layer, which will improve properties which are dependent upon low emissivity; or it may serve to reduce the number of oxygen holes in the layer, thus increasing the emissivity of the coating for certain alternate applications.

The procedure used for heat treating the coated substrate may vary. In one embodiment the treatment consists of placing the coated substrate into a heated enclosure under controlled atmospheric conditions for a predetermined period, depending upon the temperature chosen for the enclosure and the nature of the atmosphere utilized. In order to improve those properties dependent upon low emissivity values, this heat treatment takes place in a reducing atmosphere, which may be identical with that of the float bath, i.e. 90% nitrogen and 10% hydrogen or, optionally, a neutral atmosphere.

By heat treating the coated substrate in a reducing or neutral atmosphere, an anionic doping effect is produced which is favorable to increasing the electrical conduction and infrared reflection of the layer. Depending upon the time interval and temperature selected, the density of the charge carriers can be varied considerably from, for example, $1 \times 10^{20}$ to $15 \times 10^{20}$ carriers per cm$^3$. The mobility of the charge carriers may also be varied, for example, from 10 to 50 cmV$^{-1}$s$^{-1}$.

The heat treatment described above may be performed immediately after the formation of the oxide layer, directly on the glass production line as, for example, in an annealing lehr, to advantageously incorporate the heat of the glass into the process. Alternatively, this step may also be performed later in a separate installation on the glass production line, such as an attached tunnel lehr or a tempering or bending line.

In performance of this heat treatment, the coated substrate must be heated to a temperature of at least 300° C., keeping in mind that the temperature chosen must be compatible with the substrate. The duration of this heating step is adjusted depending upon the temperature chosen, as well as the composition of the reducing atmosphere and it may range from a few seconds to several hours. The item is then cooled to a temperature no higher than 300° C. until contact with an oxidizing atmosphere no longer alters the performance of the layer. In cases where the treatment is performed simultaneously with the tempering of the glass, the nozzles which supply the tempering gasses may also be connected to sources supplying the reducing or neutral gas necessary for the treatment.

The efficiency of the heat treatment increases with:
the reducing nature of the atmosphere in the heating enclosure. For example, with the percentage of hydrogen in a mixture of $N_2 + x\%$ $H_2$ wherein X is a positive real or 0, most advantageously when X ranges between 0 and 10 for a treatment improving the low emissivity properties the temperature, advantageously ranging between 300° and 650° C.; and the time chosen for the treatment, which can range between a few seconds and several hours, depending upon the temperature chosen and the composition of the atmosphere used within the enclosure.

Alternatively the heat treatment in an enclosure may be performed in an oxidizing atmosphere in order to increase the emissivity of the coating.

In an other embodiment of this heat treatment process, the oxide may either be reduced until a metal or, conversely, substoichiometric metal oxide/layer may be oxidized by passing the coated substrate through a reducing, or alternatively, an oxidizing burning steam respectively. Advantageously, the coated substrate is subjected to this intense heating for a period of less than one second. Depending upon whether one chooses a reducing or oxidizing gas mixture for the burner jet, one may increase, or, on the contrary, reduce those properties of the layer thus treated which depend upon low emissivity.

By utilizing the process described above, the average temperature reached by the substrate may be as low as 70° C. if the burner is arranged so that the flame impinges upon the substrate only on the coated side. This assures that a previously tempered glass substrate retains its tempering level and that heat-sensitive substrates manufactured of a material other than glass or comprising, in addition to the glass, other materials such as polyvinyl butyrals (PVB's) are not adversely affected.

The burner utilized for treating the coating layer, which is described in detail below, is fed a mixture of comburent gas (e.g. oxygen or a mixture of a neutral gas and oxygen) and a combustible gas containing hydrogen and/or carbon (e.g. hydrogen, carbon monoxide or a gaseous alkane, alkene or alkyne). The proportions of the comburent and combustible gasses are not stoichiometric. On the contrary, the mixture contains an excess of a reducing gas or an oxidizing gas, depending upon whether a reducing treatment or an oxidizing treatment is desired. The burner described below may be, for reasons of safety and ease of use, a linear burner with outside gas mixing.

The burner 10 is of the type shown in the accompanying drawing figure. It is constructed of two chambers 12, 14 for the introduction of the combustible and comburent gases, which are fed into burner 10 by pipes 16 and 18. Each of chambers 12, 14 is provided with access vents 20, 22 to the surface of burner 10. Vents 20 which permit the flow of gas from upper chamber 14 communicate with chamber 2 by means of pipes 24 which pass through lower chamber 12 in an airtight configuration.

In order to promote an effective mixing of the combustible and comburent gasses, vents 20 and 22 are oriented in a zig-zag configuration on the surface of burner 10. If burners of a greater length are necessary for a particular application, a deflector (not illustrated) may be provided or chambers 12 and 14 may be constructed with a beveled shape in order to assure an equality of distribution of the gasses from one end of burner 10 to the other. Burners of this type are manufactured by the French company AIR LIQUIDE under the trade name "FMT burners"

As noted above, after spraying the indium formate powder on the surface of the substrate, alone or in combination with tin compounds such as dibutyltin oxide and dibutyltin fluoride, the resulting coating is too oxidized to have good low emissivity and low resistivity characteristics, and a heat treatment of the coated substrate is necessary to improve these characteristics. The proportions of oxidizing or reducing gasses chosen for the treatment is a function of the emissivity and resistivity desired, as well as the nature of the gasses and the operating conditions chosen.

One may experimentally determine, for the operating conditions existing at a given installation (e.g. the speed with which the substrate passes the burners and distance of the substrate from the burners) the necessary proportions of the gaseous reactants needed to reduce the layer totally to the metallic state. The attainment of this metallic state is recognizable due to the fact that once it is reached, the layer changes in appearance, acquiring a certain mirror-like reflectivity in the visible spectrum and in some cases, particularly for transformed indium oxide, the coating may begin to lose its adherence to the substrate.

This experimental process comprises adjusting the respective proportions of the oxidizing and reducing gasses so as to provide a mixture that contains slightly more reducing gas (i.e. approximately 10%) than the amount necessary for a stoichiometric mixture. Thereafter, various coated samples are subjected to the flame treatment while gradually adjusting the components of the mixture toward stoichiometric proportions, until the coating layer is reduced to the metallic state. The proportions of the gasses necessary to achieve this transition are noted and one need simply reduce the delivery of the reducing gas from this level to attain the desired level of emissivity and reflectivity for the coating.

EXAMPLES

The following examples are set forth for the purpose of illustration only and are not to be construed as limiting the scope of the invention in any manner.

Examples I–III illustrate the relative proportions of oxygen and hydrogen necessary to effect the heat treatment of a coated substrate while passing the substrate at various speeds through the heating chamber.

EXAMPLE I

A substrate, coated with a powder comprising an indium oxide base, was passed 1 cm. under the linear burner depicted in the drawing figure at a speed of 3 cm./second.

In order to obtain optimal emissivity and resistivity properties, the following gas delivery rates were required:

oxygen 1.9 liters/minute/1 cm. of burner length
hydrogen 4.0 liters/minute/1 cm. of burner length

EXAMPLE II

Under the same conditions described in Example I, an increase in the speed at which the substrate passes under the burner, to 5 cm./second, requires the following gas delivery rates in order to obtain optimal emissivity and reflectivity:

oxygen 2.3 liters/minute/1 cm. of burner length
hydrogen 4.7 liters/minute/1 cm. of burner length

EXAMPLE III

When the speed of the substrate is increased further to 20 cm/second while the other parameters described in Examples I and II are unchanged, the following gas delivery rates were required:

oxygen 6.0 liters/minute/1 cm. of burner length
hydrogen 13.0 liters/minute/1 cm. of burner length Examples IV-VIII depict the properties obtained with a composite coating comprising a layer of indium formate powder mixed with 4% by weight of dibutyltin oxide. The heat treatment of the coated substrate in Examples IV-VI was carried out using the first method described above, i.e. maintaining the coated substrate in a heated enclosure under a controlled atmosphere. Examples VII and VIII utilized the second method of heating to treat the coating described in Examples V and VI, i.e. utilizing a linear burner such as the one depicted in the drawing figure

EXAMPLE IV

A powder comprising an indium formate base was mixed with 4% by weight of dibutyltin oxide and distributed upon a glass ribbon traveling at 18 meters/minute, whose surface temperature was maintained at 600° C.

After the resultant pyrolysis of the powder, the coated substrate was subjected to a heat treatment consisting of an annealing in an enclosure at 600° C. for two minutes under a nonoxidizing nitrogen atmosphere, and then gradual cooling to 300° C. for two minutes while being maintained in the nitrogen atmosphere.

The following properties were observed:

|  | Before heat treatment | After heat treatment |
| --- | --- | --- |
| Thickness (angstroms) | 900 | 900 |
| Aver. Coef. of IR reflection | 0.33 | 0.70 |
| Emissivity | 0.67 | 0.30 |
| Transmission energy factor (%) | 74.5 | 76.0 |
| Light transmission factor (%) | 74.3 | 79.0 |
| Square resistance (ohms) | 205 | 35 |

EXAMPLE V

This experiment was performed under the same conditions as Example IV, except that the thickness of the layer deposited upon the substrate was increased to 1900 angstroms. The following properties were observed for this coated substrate:

|  | Before heat treatment | After heat treatment |
| --- | --- | --- |
| Thickness (angstroms) | 1900 | 1900 |
| Aver. Coef. of IR reflection | 0.53 | 0.87 |
| Emissivity | 0.47 | 0.13 |
| Transmission energy factor (%) | 77 | 72 |
| Light transmission factor (%) | 81.3 | 83.0 |
| Square resistance (ohms) | 92 | 11 |

EXAMPLE VI

This experiment was performed under the same conditions as Examples IV and V, except that the thickness of the layer deposited upon the substrate was increased to 3000 angstroms. This produced a layer which was mauve red in reflection and slightly green in transmission, with the following properties:

|  | Before heat treatment | After heat treatment |
| --- | --- | --- |
| Thickness (angstroms) | 3000 | 3000 |
| Aver. Coef. of IR reflection | 0.76 | 0.89 |
| Emissivity | 0.24 | 0.11 |
| Transmission energy factor (%) | 78.8 | 66.0 |
| Light transmission factor (%) | 85.8 | 82 |
| Square resistance (ohms) | 25 | 7.5 |

EXAMPLE VII

This experiment utilized the same coating described in Example V prior to the heat treatment step. The coated substrate was then subjected to the flame from a burner of the type described previously. The burner was fed with a mixture of hydrogen and oxygen as described above.

Upon matching the required gas delivery rate with the speed of the coated substrate passing beneath the burner flame (see Examples I - III), a coating with the same properties as that in Example V was thereafter obtained.

EXAMPLE VIII

The coating described in Example VI was deposited upon a glass ribbon, which was then subjected to a heat treatment process as described in Example VII.

A coating with the same properties as described in Example VI was thereafter obtained.

These comparative Examples conclusively illustrate that the selection of either heat treatment process leads to the formation of a coating upon the substrate with optimal emissivity and resistivity properties.

Whichever method of heat treatment one selects for the substrate, the heating step may either be performed immediately after the production and subsequent coating of the glass, for example, on the same float line, or it may be performed later. This is normally the case when the glass substrate must be tempered or laminated after the coating has been pyrolytically deposited.

By utilizing either of the two proposed heat treatments with coatings comprising a mixture of indium formate and either dibutyltin oxide or dibutyltin fluoride, a coating layer may be formed having an electrical resistivity on the order of $2 \times 10^{-4}$ cm. By modulating the intensity of the heat treatment, it is also possible to obtain layer performances intermediate between those of an untreated layer and those measured for a layer which has undergone the most intense heat treatment.

Alternatively, it is also possible to increase the emissivity and resistivity of the layer during the heating process. Thus the resistance of a coated substrate having a square resistance of 15 ohms may be increased to 16 ohms, or 2,000 ohms by passing the substrate 1 cm. beneath the burner at 10 cm./second or 6 cm./second respectively. The gas flow rates utilized to provide these values was 2.4 liters per minute per cm. of burner length for oxygen and 3.0 liters per minute per cm. of burner length for hydrogen. The same effect may be obtained by utilizing the first heating procedure described herein in an oxidizing, rather than a reducing atmosphere.

It is also possible with either proposed mode of heat treatment to create, on the same coating, zones of different electrical conduction by the application of different heat treatments. This kind of differentiated heat treatment by zones, on the same coating, is particularly easy when the second type of heat treatment is used. For this purpose, the conditions of exposure of the layer to the heating means are modified locally.

To create this effect, the speed with which the coated substrate to be treated passes the burner is varied as a function of the desired result. With a burner placed crosswise in relation to the direction of travel of the substrate, layers with crosswise strips having differentiated properties may be obtained by modulating the passing speed of the substrate.

It is also possible to obtain lengthwise strips in the direction of movement of the substrate with different electrical and optical characteristics by adding additional burners opposite these zones or by performing the treatment over the entire width of the substrate with a plurality of burners adjusted differently from one another.

These heat treatments, and in particular those performed by the second method utilizing the burners discussed above, are therefore particularly suited to the production of coatings with layers having zones with differentiated electrical, thermal and optical properties. Thus, for example, heated coatings can be produced with thin layers having varying resistances, depending upon which zone of the coating one examines.

Alternative methods may be utilized to carry out the heating process described above. For example, a microwave plasma torch fed by reducing or, on the contrary, oxidizing gas, either to reduce the oxide and lower the emissivity or resistivity of the layer, or, on the contrary, to oxidize the metal and increase the emissivity or resistivity of the layer, may also be utilized.

The second method of heat treatment is therefore particularly suited to the production of thin-layer coatings for motor vehicle glazings with a high level of temper or laminated and enclosing a sheet of plastic, such as a P.V.B interlayer. Even if coated and treated according to the invention, the glazings can be sufficiently tempered to meet the United Nations Regulation No. 43 for the approval of motor vehicle glazings. In spite of the tempered treatment the emissivity and the resistivity of these coatings have a good level. The emissivity of these coatings is less than 0.15 for a thickness around 1800 to 1900 Angstroms, and the resistivity is less than $3 \times 10^{-4}$ ohm. cm.

The pyrolytically deposited coatings of the present invention have many other practical uses, as in, for example, low-emissive glazings, heated glazings and, in general, glazings making use of the variable optical and/or electrical properties of the coatings for the building trade; and, as noted earlier, for safety laminates in automotive glass or for auto glass which makes use of the electrical conductivity of the coating to trigger a burglar alarm when a window is broken, or which constitutes a radio antenna.

The coating of the invention may also be advantageously applied onto various substrates, in particular, for insulating glass articles such as bottles, vials, various types of glassware, optical elements, fiberglass and articles comprised of silica, alumina or refractory materials. Standard powder spray guns are used to spray the powder or mixture of powders onto the substrates described above, (not the nozzles described in French patent application Nos. 2,542,636 and 2,542,637, discussed earlier).

The indium formate based powders of the invention need not necessarily be used in solid form. For example, the powder can be solubilized, i.e. in methanol, and the solution may be sprayed directly onto a substrate whereupon it is pyrolyzed and forms a metal oxide layer that can undergo a heat treatment by one of the methods described above in order to modify the characteristics of the layer.

The heat treatments performed after the deposition of the layer have been described as being applied to a layer of indium oxide, whether doped or not with tin, and obtained by the pyrolysis of a powder with an indium formate base; but this treatment can also be successfully applied to any layer with an indium oxide base, whether doped or not with tin or other material, obtained in another way; for example, liquid pyrolysis, CVD (chemical vapor deposition), or a vacuum technique, whether the initial compound is formate or not.

These heat treatments can even be applied to any other comparatively low melting metal layer which, like the layer with an indium oxide base, is nonstoichiometric, thus including, for example, layers with a base of vanadium, zinc, tin oxide, etc. These heat treatments can even make it possible to obtain metal layers from metal oxide layers as an end result. Moreover, the heat treatments may also be used to recrystallize a poorly crystallized or amorphous layer, in order to modify its electronic properties.

While it is apparent that the invention herein disclosed is well calculated to fulfill the objectives above stated, it will be appreciated that numerous modifications and embodiments may be devised by those skilled in the art, and it is intended that the appended claims cover all such modifications and embodiments as fall within the true spirit and scope of the present invention.

We claim:

1. A method for coating a substrate with a pyrolyzed metal oxide coating which comprises depositing a predetermined amount of dry indium formate of the formula In (HCOO)$_3$ upon a surface of a heated substrate so as to pyrolyze said indium formate and form a coating of indium oxide upon the surface of the substrate.

2. The method of claim 1 wherein the indium formate is deposited as a powder.

3. The method of claim 1 which further comprises selecting the substrate from the group consisting of glass, metal, ceramic and other refractory materials.

4. The method of claim 3 wherein said glass substrate is heated to a temperature below about 650°–700° C. prior to the deposition of indium formate upon the surface of the substrate.

5. The method of claim 1 which further comprises mixing the indium formate with at least one compound having a decomposition temperature on the same order as that of indium formate prior to depositing the mixture onto the surface of the heated substrate.

6. The method of claim 5 wherein the compound is selected from the group consisting of powdered or gaseous tin compounds and gaseous organotin compounds.

7. The method of claim 6 wherein the powdered tin compounds are selected from the group consisting of dibutyltin oxide and dibutyltin fluoride.

8. The method of claim 7 wherein the powdered tin compounds are mixed with the indium formate in proportions ranging from about one to about thirty percent by weight.

9. The method of claim 6 wherein the gaseous tin compound is $SnCl_4$.

10. The method of claim 6 wherein the gaseous organotin compound is $BuSnCl_3$.

11. A method for forming a transparent electroconductive coating on a substrate which comprises.
preparing a dry metal composition containing indium formate of the formula $In(HCOO)_3$;
depositing said composition onto a surface of a heated substrate with coating means so as to pyrolyze the composition; and
heating the coated substrate to enhance the properties of the layer.

12. The method of claim 11 which further comprises mixing at least a powdered or gaseous tin compound or a gaseous organotin compound with the indium formate prior to depositing the metal composition upon the substrate.

13. The method of claim 12 wherein the powdered tin compounds are selected from the group consisting of dibutyltin oxide and dibutyltin fluoride.

14. The method of claim 13 wherein the powdered tin compounds are mixed with the indium formate in amounts ranging from about one to about 30 percent by weight.

15. The method of claim 12 wherein the gaseous tin compound is $SnCl_4$.

16. The method of claim 12 wherein the gaseous organotin compound is $BuSnCl_3$.

17. The method of claim 12 wherein the mixture is deposited upon the substrate as a powder.

18. The method of claim 17 which further comprises suspending the powdered mixture in a stream of carrier gas prior to depositing it onto the surface of the substrate.

19. The method of claim 12 wherein the coated substrate is heated by maintaining said substrate in a heated enclosure at a temperature of at least about 300° C. in a reducing atmosphere for a predetermined time period to enhance the properties of the layer and to form a metal coating upon the substrate.

20. The method of claim 12 wherein the coated substrate is heated by maintaining said substrate in a heated enclosure at a temperature of at least about 300° C. in an oxidizing atmosphere to form a metal oxide coating upon the substrate with modified properties compared with the coating as deposited.

21. The method of claim 12 wherein the substrate is heated by subjecting a coated side of the substrate to an intense heating for a period of less than about one second.

22. The method of claim 12 wherein the heat treatment may be performed upon the coated substrate on the line for manufacturing coated glass.

23. The method of claim 12 wherein a coated glass substrate is tempered or laminated prior to subjecting the coated substrate to a heat treatment.

24. The method of claim 21 wherein preselected areas of the coating are exposed to different degrees of heating so as to obtain a coating layer having portions with different properties.

25. The method of claim 21, wherein the substrate is heated by subjecting a coated side of the substrate to the flame of at least one burner fed with gas either reducing or oxidizing according to the either reducing or oxidizing treatment desired.

26. A method for coating a substrate with a pyrolyzed metal oxide coating which comprises:
reacting an indium compound with an inorganic acid to form an indium salt;
reacting the indium salt with ammonia to form an indium hydroxide precipate;
reacting the precipitate with formic acid to obtain indium formate;
depositing a predetermined amount of said indium formate in dry form upon the surface of a heated substrate so as to pyrolyze said indium formate of the formula $In(HCOO)_3$ and form a coating of indium oxide upon the surface of said substrate.

* * * * *